United States Patent [19]

Raschle

[11] 4,148,178

[45] Apr. 10, 1979

[54] DEVICES FOR DETERMINING THE HELIX ANGLE OF TWISTED THREADS DURING FALSE-TWIST TEXTURING

[75] Inventor: Josef Raschle, Bütschwil, Switzerland

[73] Assignee: Heberlein Maschinenfabrik AG, Switzerland

[21] Appl. No.: 895,436

[22] Filed: Apr. 11, 1978

[30] Foreign Application Priority Data

Apr. 14, 1977 [CH] Switzerland ............... 4671/77

[51] Int. Cl.$^2$ ............... D02G 1/02; G01N 33/36; G01L 5/06
[52] U.S. Cl. ............................. 57/264; 57/284; 73/160
[58] Field of Search ............... 57/1 R, 34 R, 34 HS, 57/77.3–77.45; 73/158–160

[56] References Cited

U.S. PATENT DOCUMENTS

| | | | |
|---|---|---|---|
| 2,715,382 | 8/1955 | Kreamer | 57/1 R UX |
| 3,405,556 | 10/1968 | Gonsalves et al. | 73/160 |
| 3,613,347 | 10/1971 | Carruthers | 57/1 R |
| 3,667,292 | 6/1972 | Hada | 73/160 |
| 3,705,487 | 12/1972 | Carruthers | 57/77.4 |
| 4,015,414 | 4/1977 | Sholly, Jr. | 57/34 HS |

Primary Examiner—John Petrakes
Attorney, Agent, or Firm—Larson, Taylor & Hinds

[57] ABSTRACT

Devices are described for determining the helix angle of twisted threads during false-twist texturing. The thread passes over a convex spherical surface at the top of a two-armed lever pivoted between the arms and having a vertical zero position. Magnetic means act on the lower arm to bias the lever to the zero position. In one device the lever is pivoted about a diameter of a vertical cylindrical tube rotatable on a second vertical tube, a scale being provided to indicate the position of the tube about its axis which, in turn, depends on the helix angle of the thread traversing the spherical surface, which has a radius of curvature equivalent to the length of the upper lever arm. In another device the two-armed lever is carried by a ball in a spherical bearing and has a pointer at the lower end that indicates the position of the lever with respect to polar co-ordinates on a flat surface. The lower arm may be arranged selectively to cover photo-electric devices connected to maintain the twist density of the thread at processing positions of a friction texturing machine operating on the false-twist texturing principle. The magnetic biasing may be effected by permanent magnets or for greater sensitivity by an electro-magnet fed with discrete pulsations.

11 Claims, 7 Drawing Figures

DEVICES FOR DETERMINING THE HELIX ANGLE OF TWISTED THREADS DURING FALSE-TWIST TEXTURING

FIELD OF THE INVENTION

The invention relates to a device for determining the helix angle of twisted threads during the insertion of false twist.

The texturing of threads or bundles of threads of thermoplastic material by false twisting and thermosetting in an uptwisted condition calls for the use of various false-twist insertion devices whose purpose it is to introduce temporarily a specific amount of twist density into the threads. The size and regularity of the twist density that has been introduced into the threads exercises a decisive influence on the quality of the textured yarn, and it is therefore essential for the machine builder and the yarn texturer to use test instruments permitting the twist density to be checked during false twisting.

DESCRIPTION OF THE PRIOR ART

With conventional false-twist insertion devices, i.e., pin spindles, there is a simple direct relationship between the rotational speed of the insertion device and the twist density and the performance of the false-twist insertion device may to a large extent be assessed by measuring the rotational speed. With friction false-twist insertion devices, there is, however, no means of deducing the twist density from the machine settings directly. For these reasons it is very difficult to check the twist density.

There is in existence a well-known process whereby a thin blade mounted on a lever and pivoting slightly about its own axis is used to determine the amount of twist in the yarn continuously. The blade is pressed against the twisted thread, friction developing between the blade and the thread so that the lever rotates about its own axis until the blade adopts the contours of the twist in the yarn. Even this method has failed to produce to date any practical results in operation particularly since the device reacts very sensitively to the slightst disturbance owing to the lack of stabilizing forces.

A friction device for the continuous determination of twist in yarn is known, featuring a cylinder pivoting freely about its own axis, the yarn running across the surface of the cylinder diagonally to the axis. If the line formed by the helix angle of the twisted thread is parallel to the axis of the cylinder, then the cylinder is not caused to rotate about its own axis. However, if the line formed by the helix angle of the twisted thread deviates from the axis of the cylinder, then the cylinder is caused to rotate in one or the other direction. The rotation of the cylinder activates an indicator or regulator through an electric circuit. The disadvantage of this device is described below in the description of the accompanying drawings.

SUMMARY OF THE INVENTION

The object of the invention is to create a device for determining the helix angle of twist threads with high sensitivity and to eliminate the disadvantage of the aforesaid known devices.

According to the invention a device for determining the helix angle of twisted threads comprises a lever with two arms having a body presenting a spherical surface at the end of the first arm, the radius of the surface being equivalent to the length of this arm, means for biasing the second lever arm towards an initial position, means for guiding the thread over the spherical surface so that the thread is fed at a tangent to the surface and delivered at a tangent from the surface, and a device for indicating the helix angle of the twisted thread as a function of the deviation of the second arm from the initial position.

The invention also includes the additional employment of this device as an integral part of a system for monitoring the density of twist of threads at the processing positions of a friction texturing machine operating on the false-twist texturing technique.

An important advantage of the invention is that a very high degree of sensitivity may be attained by the selection of a relatively long lever and a relatively low lever mass.

DESCRIPTION OF THE DRAWINGS

In order that the invention may be clearly understood and readily carried into effect, devices in accordance therewith will now be described, by way of example, with reference to the accompanying drawings, in which.

Figure 1:
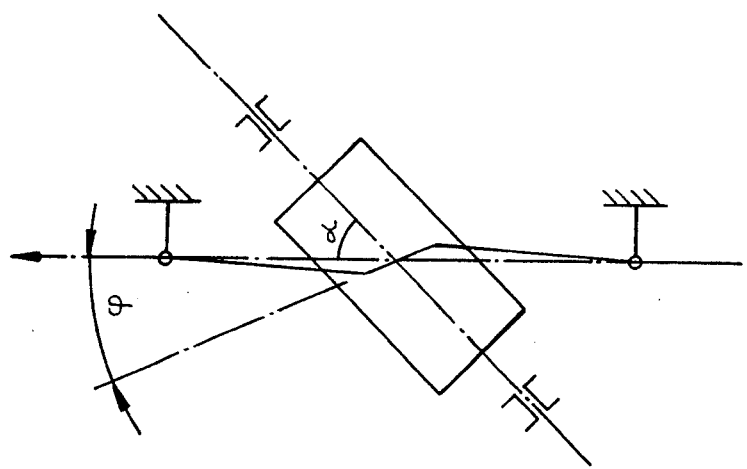
FIG. 1 is a diagrammatic plan view of a known device for determining the helix angle of twisted threads.

In the known device of FIG. 1, thread runs across the surface of a cylinder diagonally to the cylinder axis. The cylinder is freely pivoted about its axis. If the line formed by the helix angle of the twisted thread is parallel to the cylinder axis, the cylinder is not caused to rotate about its axis. However, if the line formed by the helix angle of the twisted thread deviates from the axis of the cylinder, then the cylinder is caused to rotate in one direction or the other.

The disadvantage of this device is that the thread running diagonally over the surface of the cylinder shows a constant tendency to seek the smallest angle of wrap and to adopt a path as represented in FIG. 1, the angle $\phi$ being the deviation of the path of the thread over the cylinder from the line joining the points at which the thread is delivered to the cylinder and received from it.

If the thread is to be regulated to a specific density of twist, i.e., to a specific helix angle, than the same angle $\alpha$ must also be set between the axis of the cylinder and the line joining the said feeding and delivery points. If the direction in which the thread runs over the surface of the cylinder changes under the influence of the thread tension so that this direction makes with the axis of the cylinder the angle $\alpha$ plus $\phi$, then the density of twist is no longer regulated to the helix angle $\alpha$, but to the angle $\alpha$ plus $\phi$, $\phi$ being variable.

Figure 2:
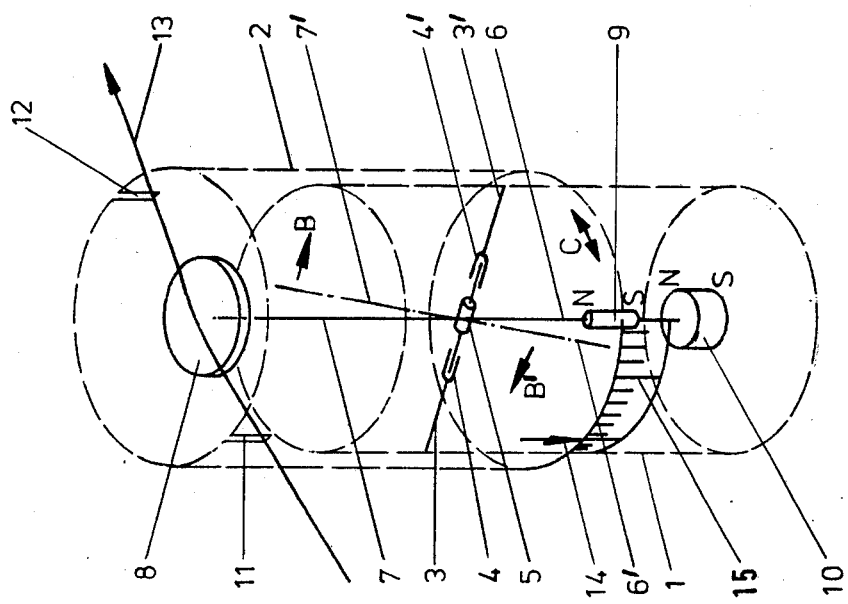
FIG. 2 is a perspective view of a first example of a device constructed in accordance with the invention.

The device shown in FIG. 2, comprises two telescopic cylindrical tubes 1, 2, the interior of the cylindrical tube 1 containing holders, 3, 3' on which are mounted bearings 4, 4' for supporting the axis of rotation 5 of a twin lever 6, 7. The tube 2 is rotatable about its axis on the tube 1 which is fixed. Mounted at the end of the top lever arm 7 is a body having a convex spherical upper surface 8 whose radius is equivalent to the length of the lever arm 7. Mounted at the end of the bottom lever arm 6 is a permanent bar magnetic 9, with one of its poles facing the opposite pole of a bar magnet 10 at the bottom of the cylindrical tube 1.

The cylindrical tube 2 has on its uppermost edge two diametrically opposite slots 11, 12, for guiding thread over the spherical surface, the thread being fed and delivered at a tangent to this surface.

The cylindrical tube 2 has on its lowermost edge a reference index 14, its position about the tube axis being indicated by a scale 15 on the circumference of the fixed cylindrical tube 1.

Figure 3A:
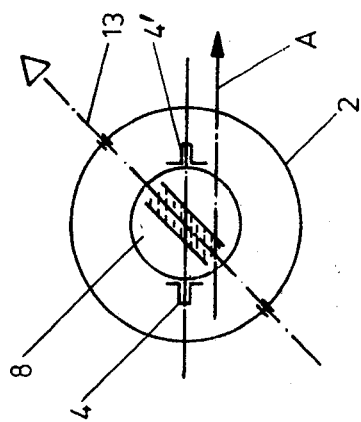
FIGS. 3a and 3b are plan views of the device of FIG. 2 respectively showing two operative conditions of the device.
Figure 3B:
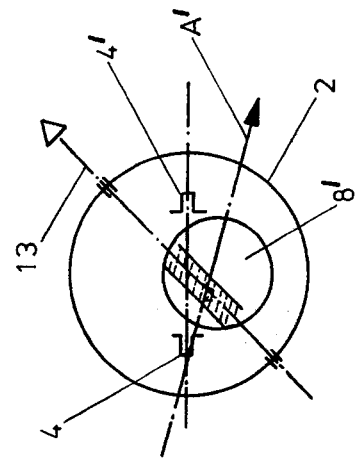

FIG. 2 shows the twin lever 6, 7, in its initial or zero position with its longitudinal axis coinciding with that of the co-axial cylindrical tubes 1, 2. The twin lever 6, 7 is held in this position by the bar magnets 9, 10 attracting each other. The thread 13 is introduced through the slot 11 in the cylindrical tube 2, passes over the pole of the spherical surface 8 and is withdrawn through the slot 12 in the cylindrical tube 2. If, as shown in FIG. 3a, the line formed by the helix angle (arrow A) of the twisted thread runs parallel to the axis of rotation 5 of the lever 6, 7, then the lever 6, 7 remains in its initial position. However, if, as shown in FIG. 3b, the line formed by the helix angle (arrow A') of the twisted thread deviates from the direction of the axis of rotation 5, then overcoming the magnetic attraction of magnets 9, 10, the lever 6, 7 is rotated about its own axis of rotation 5 and shifted to a position in the direction of the axes B, B' as indicated in FIG. 2 by the axis 6', 7', the spherical surface assuming the position 8' in FIG. 3b. The cylindrical tube 2 can now be rotated manually in the direction of the double arrow C, in relation to the cylindrical tube 1, which is maintained stationary, until the lever 6, 7 returns to its initial position. With the aid of the reference mark 14, the helix angle of the twisted thread 13 may be read off the scale.

It is further possible to pre-select the helix angle on the device of FIG. 2 and to adjust the individual working positions of a false-twist texturing machine to keep the twisted thread showing the correct helix angle.

Figure 4:
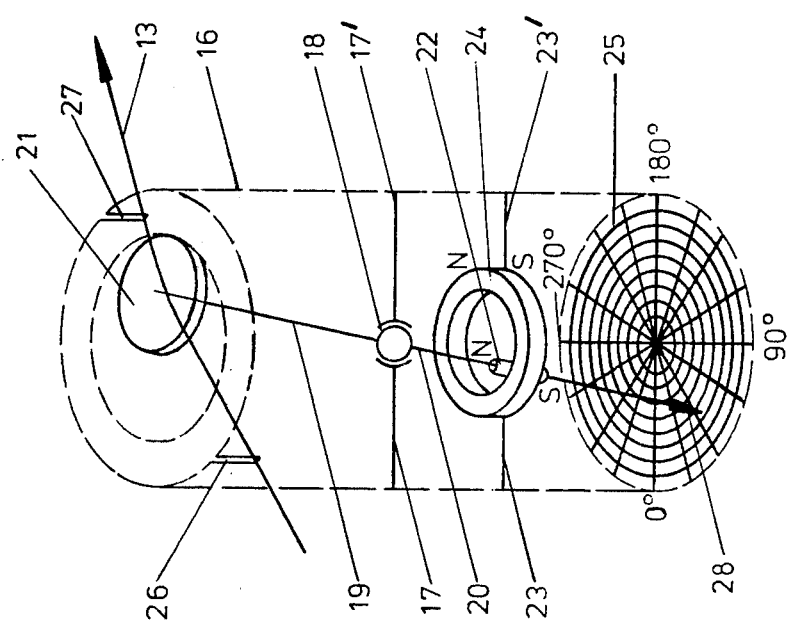
FIG. 4 is a perspective view of a second example of a device constructed in accordance with the invention.

In the example shown in FIG. 4, the device comprises a cylindrical tube 16, its interior containing holders 17, 17' for a self-aligning ball-bearing 18 supporting a twin lever 19, 20. Mounted at the top end of the lever arm 19 is a body having a spherical surface 21, its radius being equivalent to the length of the lever arm 19. Mounted roughly centrally at the bottom end of the lever arm 20 is a permanent bar magnet 22.

The cylindrical tube 16 is additionally provided internally with holders 23, 23' for a permanent ring magnet 24 and at its lower end with a glass disc 25 with polar-coordinate calibrations. The initial position of the twin lever 19, 20 is coaxial with the axis of the cylindrical tube 16. The twin lever 19, 20 is held in this position by the permanent magnets 22, 24 repelling one another. The twisted thread 13 is introduced and withdrawn through diametrically opposite slots 26, 27 in the uppermost edge of the cylindrical tube 16 as it passes over the spherical surface 21. The arms 19, 20 assume a position as represented in FIG. 4, the helix angle of the twisted thread 13 being indicated directly on the polar coordinates on the glass disc 25 beneath a pointer 28 at the end of the lever arm 20.

Figure 5:
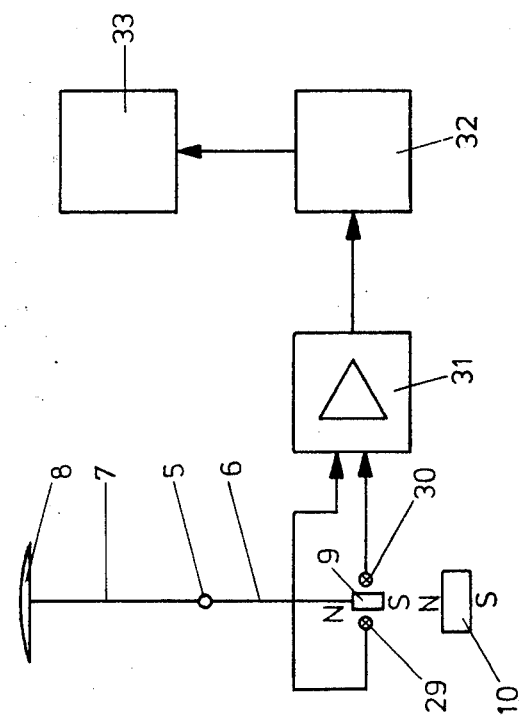
FIG. 5 is a schematic representation of a system incorporating a device constructed in accordance with the invention.

FIG. 5 shows a system by which the invention can be applied to regulating the density of twist on a friction false-twist texturing machine, by using a variant of the design shown in FIG. 2. Two photo-electric devices 29, 30 are obscured selectively in accordance with the position of the bar magnet 9.

The reference densities are set by selecting the helix angle of the twisted thread by the device shown in FIG. 2. Should the density of twist be above or below the tolerance limits of the reference setting, the lever 6, 7 is rotated in either one direction or the other, obscuring either one photo-electric device or the other to a greater or a lesser extent and transmitting corresponding signals to an amplifier 31. The output voltage of the amplifier 31 activates an actuator 32 on the friction false-twist texturing device 33 to correct the helix angle deviation and with it the twist density. Once the desired twist density has been reached, the lever 6, 7 returns to its initial position, thereby completing the regulating cycle.

Figure 6:
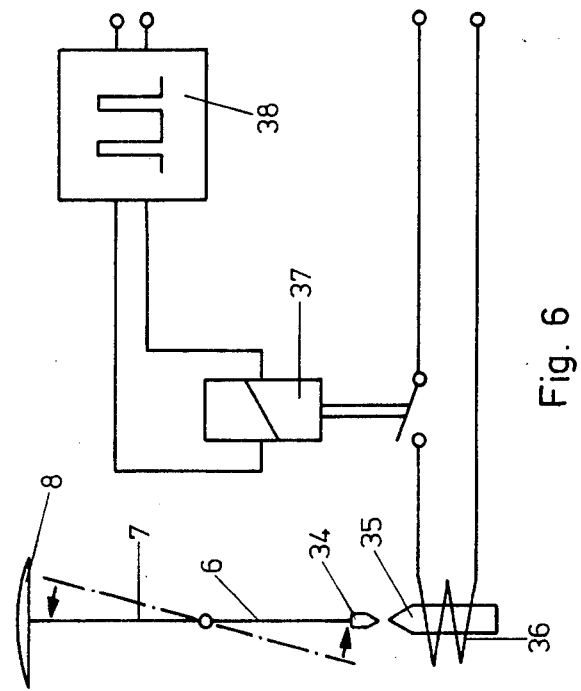
FIG. 6 is a schematic representation of another system incorporating a device constructed in accordance with the invention.

FIG. 6 shows another variant of the design shown in FIG. 2 for high sensitivity indication of twist-density deviations from a desired helix angle. In this variation of FIG. 2, the permanent magnets at the end of the lever arm 6 and at the bottom of the cylindrical tube 1 are replaced with a two-part moving-iron system 34, 35, the part 35 being provided with an induction coil 36 so as to form an electromagnet energized through a circuit breaker 37 receiving pulses at intervals of approximately 5 to 6 seconds from a pulse generator 38. Thus the lever 6, 7 is periodically zeroed and the magnetic restoring force is cancelled in the intervals between pulses. This results in the lever 6, 7 reacting with greater sensitivity to the twist density deviations of the twisted thread from the pre-selected helix angle. In this case, too, the helix angle is manually pre-selected on the device before being put into operation.

I claim:

1. A device for determining the helix angle of twisted threads during false-twist texturing, the device including a lever unit comprising a bearing member, a first lever arm extending upwards from said bearing member, and a second lever arm, coaxial with said first lever arm, extending downwards from said bearing member, and the device further including a body fixed to the top of said first lever arm, said body being formed with an upper convex spherical surface having a radius of curvature substantially equal to the distance between said surface and said bearing member, and said surface being symmetrically disposed with respect to said first lever arm, universal bearing means supporting said bearing member permitting said lever unit to swing in any direction about a point from a zero axial position wherein said arms are vertical, means operative on said second arm for biasing said lever unit to said zero position, means for guiding a travelling length of twisted thread tangentially to said spherical surface and for guiding said thread tangentially from said spherical surface after travelling over said spherical surface, and means for indicating the helix angle of said twisted thread as determined by a deviation of said lever unit from said zero axial position under the action of said thread.

2. A device according to claim 1, in which said bearing member is pivotally mounted about an axis in said bearing means, said axis being fixed transversely with respect to said lever unit and said bearing means being arranged for said axis to rotate about said zero axial position.

3. A device according to claim 2, in which said bearing means comprises a vertical cylindrical tube with said axis extending diametrically across said tube, and said device also comprising a second vertical cylindrical tube with said first-mentioned tube mounted telescopically with respect to and rotatable on said second tube.

4. A device according to claim 1, in which said bearing member is a self-aligning ball bearing and said bearing means comprise a spherical bearing therefor.

5. A device according to claim 1, comprising a vertical cylindrical tube with said bearing means mounted therein and locating said zero axial position coaxially in said tube, said guiding means being located at an upper portion of said tube and said indicating means including a graduated surface at the lower end of said tube.

6. A device according to claim 5, comprising a second vertical cylindrical tube, said first-mentioned vertical tube being mounted telescopically with respect to said second vertical tube and rotatable thereon, and said indicating means comprising an index mark on one of said vertical tubes and a scale extending circumferentially along the surface of the other said tube to be traversed by said index when said first-mentioned tube is rotated on said second tube.

7. A device according to claim 1, in which said biasing means comprise a first permanent magnet mounted on said second arm and a second permanent magnet fixed with respect to said zero axial position and interacting with said first permanent magnet to bias said lever unit to said zero axial position.

8. A device according to claim 1, in which said biasing means comprises an iron part on said second arm and an electromagnet arranged to exert a magnetic force on said iron part.

9. A device according to claim 8, comprising means for transmitting electric pulses to said electromagnet.

10. A device according to claim 1, in combination with means for sensing the position of said second arm, and means responsive to said sensing means for maintaining the twist density of the thread at a processing position of a friction-texturing machine operating on the false-twist texturing principle.

11. A device according to claim 10, in which said sensing means comprise photo-electric devices and means on said second arm for selectively covering said devices.

* * * * *